United States Patent
Wang et al.

(10) Patent No.: US 9,238,049 B2
(45) Date of Patent: Jan. 19, 2016

(54) FORMULA OF SUPPRESSING VIABILITY OF TUMOR CELLS AND A MEDICATION THEREOF

(71) Applicant: HERBIO BIO TECH CO., LTD., Tainan (TW)

(72) Inventors: Ming-Shan Wang, Tainan (TW); Shorong-Shii Liou, Tainan (TW); I-Min Liu, Tainan (TW); Hung-Hsung Wu, Tainan (TW)

(73) Assignee: HERBIO BIO TECH CO., LTD., Tainan (TW)

( * ) Notice: Subject to any disclaimer, the term of this patent is extended or adjusted under 35 U.S.C. 154(b) by 265 days.

(21) Appl. No.: 13/886,084

(22) Filed: May 2, 2013

(65) Prior Publication Data

US 2014/0328872 A1 Nov. 6, 2014

(51) Int. Cl.
*A61K 36/074* (2006.01)
*A61K 36/06* (2006.01)
*A61K 36/236* (2006.01)
*A61K 36/484* (2006.01)
*A61K 36/07* (2006.01)

(52) U.S. Cl.
CPC ............... *A61K 36/484* (2013.01); *A61K 36/07* (2013.01); *A61K 36/074* (2013.01)

(58) Field of Classification Search
CPC .... A61K 36/00; A61K 36/074; A61K 36/236
USPC .............................................. 424/195.15, 757
See application file for complete search history.

(56) References Cited

U.S. PATENT DOCUMENTS

| | | |
|---|---|---|
| 7,254,504 B2 * | 8/2007 | Klotz et al. ..................... 702/89 |
| 2003/0194451 A1 * | 10/2003 | Cho et al. ...................... 424/728 |
| 2008/0242856 A1 | 10/2008 | Lue |
| 2011/0288061 A1 | 11/2011 | Wu |

FOREIGN PATENT DOCUMENTS

JP 2011162462 A * 8/2011

* cited by examiner

*Primary Examiner* — Chris R Tate
*Assistant Examiner* — Deborah Davis
(74) *Attorney, Agent, or Firm* — Muncy, Geissler, Olds & Lowe P.C.

(57) ABSTRACT

A formula of suppressing viability of tumor cells is disclosed. The formula comprises 27.3-50.0 wt % of *Taiwanofungus camphorates*, 27.3-40.0% of *Ganoderma lucidum* and 16.7-45.4% of *Glycyrrhiza uralesis* Fisch.

7 Claims, 7 Drawing Sheets

FORMULA OF SUPPRESSING VIABILITY OF TUMOR CELLS AND A MEDICATION THEREOF

BACKGROUND OF THE INVENTION

1. Field of the Invention

The present invention relates to a formula and, more particularly, to a formula of suppressing viability of tumor cells. The present invention further relates to a medication comprising the formula.

2. Description of the Related Art

Medical treatments for tumor are different in Western medicine and in traditional Chinese medicine. In Western medicine, surgery, radiation therapy, chemotherapy and immunotherapy are generally accepted standards. On the other hand, in traditional Chinese medicine, several traditional herbs are used as medical treatments of tumor.

*Taiwanofungus camphorates* is also called Niu Chang-Ku or Chang-Zhi. The current taxonomic position of *Taiwanofungus camphorates* is as follows: Fungi, *Basidiomycota, Basidiomycotina, Homobasidiomycetes, Aphyllophorales, Polyporaceae, Antrodia*. *Taiwanofungus camphorates* grows only on inner rotten walls of hollow materials from an endemic *Cinnamomum kanehirai*. Annual or perennial fruit bodies are vivid red, orange red or pale cinnamon and exhale smell of sassafras.

Several active ingredients, such as polysaccharides, adenosines and several triterpenoids, are found in extracts from mycelia and fruit bodies of *Taiwanofungus camphorates*. The triterpenoids, such as antcin A, antcin B, antcin C, antcin E, antcin F, methylantcinate G, methylantcin H, antrocin, 4,7-dimethoxy-5-methyl-1,3-benzodioxole and 2,2',5,5'-tetramethoxy-3,4,3',4,-bimethyl-enedioxy-6.6'-dimethylbiphenyl, are believed to possess anti-tumor activity.

In traditional Chinese medicine, *Taiwanofungus camphorates* belongs to herbs with cold property. A short-term application of *Taiwanofungus camphorates* has a significant effect on anti-inflammation, and has a better effect on protection from chronic hepatitis caused by dietary inadequacy or long-term fatigue. On the contrary, a long-term application of *Taiwanofungus camphorates* may decrease a concentration of free radicals in human body, resulting in a cold constitution with reduced immunity. For patients undergoing chemotherapy or radiation therapy, application of *Taiwanofungus camphorates* may decrease side effects of chemotherapy or radiation therapy at the beginning. However, a long-term application of high dose of *Taiwanofungus camphorates* may cause immunity reduction, such as increasing a possibility of blood infection.

SUMMARY OF THE INVENTION

It is therefore the objective of this invention to provide a formula which achieves a better effect of suppressing viability of tumor cells than a single extract of *Taiwanofungus camphorates*.

It is another objective of this invention to provide a formula which decreases side effects, such as deficiency of vital energy, due to long-term application of *Taiwanofungus camphorates*.

It is yet another objective of this invention to provide a medication of suppressing viability of tumor cells in which the formula serves as an active ingredient.

A formula comprises 27.3-50.0 wt % of *Taiwanofungus camphorates*, 27.3-40.0 wt % of *Ganoderma lucidum* and 16.7-45.4 wt % of *Glycyrrhiza uralensis* Fisch.

In a preferred form shown, the weight percentage of *Taiwanofungus camphorates* is 30.8% by weight of the formula.

In a preferred form shown, the weight percentage of *Ganoderma lucidum* is 30.8% by weight.

In a preferred form shown, the weight percentage of *Glycyrrhiza uralensis* Fisch is 38.5% by weight of the formula.

In a preferred form shown, the weight percentages of *Taiwanofungus camphorates, Ganoderma lucidum* and *Glycyrrhiza uralensis* Fisch are 30.8%, 30.8% and 38.5% by weight of the formula.

In a preferred form shown, a fruit body of *Taiwanofungus camphorates* is used as *Taiwanofungus camphorates*.

A medication of suppressing tumor cell proliferation comprises the formula mentioned above and a medical acceptable excipient.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

An embodiment of a formula according to preferred teachings of the present invention comprises: 27.3-50.0 wt % of *Taiwanofungus camphorates*, 27.3-40.0% of *Ganoderma lucidum* and 16.7-45.4% of *Glycyrrhiza uralensis* Fisch. The formula of the invention can effectively suppress viability of tumor cells.

In the embodiment, fruit bodies of *Taiwanofungus camphorates* are used because fruit bodies contain high contents of triterpenoids with benefit of anti-inflammation. In addition, fruit bodies of *Ganoderma lucidum* and roots of *Glycyrrhiza uralensis* Fisch are used in the embodiment. Fruit bodies of *Ganoderma lucidum* and roots of *Glycyrrhiza uralensis* Fisch are easily obtained, thereby reducing costs of the formula of the invention.

The formula of the invention can effectively suppress viability of tumor cells, thereby being potential to be applied to pharmaceutical industry, being an active substance of medication or health products with anti-tumor activities. In the present invention, the formula of the invention can be given to any target individually or combined with any acceptable excipients, for example carriers or other ingredients, and is capable of being further manufactured into any form of medicament, such as pill, capsule, powder, solution and pastil for easy and convenient delivery to targets.

In order to prove the formula of the invention has a better effect on suppressing viability of tumor cells, crude extracts of the formula of the invention is used to suppress viability of tumor cells in vitro and in vivo.

(A) Preparation of Crude Extracts of the Formula of the Invention

In this experiment, raw materials comprising *Taiwanofungus camphorates, Ganoderma lucidum* and *Glycyrrhiza uralensis* Fisch are blended together in given weight percentages shown in Table 1. Preferably, the raw materials are smashed into smaller particles with diameter smaller than 5 mm before the blending, thereby increasing efficiency of blending and extraction followed by.

TABLE 1

The given weight percentages of the raw materials.

| Groups | *Taiwanofungus camphorates* (wt %) | *Ganoderma lucidum* (wt %) | *Glycyrrhiza uralensis* Fisch. (wt %) |
|---|---|---|---|
| A1 | 40.0 | 40.0 | 20.0 |
| A2 | 50.0 | 33.3 | 16.7 |
| A3 | 30.8 | 30.8 | 38.5 |
| A4 | 27.3 | 27.3 | 45.4 |
| A5 | 100 | 0 | 0 |
| A6 | 0 | 100 | 0 |
| A7 | 0 | 0 | 100 |

5 kg of the raw materials are extracted by 1 liter of 95% ethanol. Mixtures shown in Table 1 are kept for reflux for 8 hours at a constant temperature of 50° C. for three time to obtain extracted mixtures. Then, the extracted mixtures are filtered, vacuum concentrated and freeze dried to obtain crude extracts. Following experiments with crude extracts are carried on:

(B) In Vitro Pharmacological Study of the Formula of the Invention

S-180 (mice sarcoma cell line), A549 (human lung tumor cell line), HepG2 (human hepatic tumor cell line), HCT-116 (human colorectal tumor cell line), and MDA-MB-231 (human breast tumor cell line) are used in this experiment. All tumor cell lines are purchased from the Food Industry Research and Development Institute in Taiwan, and cultured in medium (Dulbecco's Modified Eagle Medium) containing 10% FBS (purchased from Biological Industries, Kibbutz beit haemek), 2 mmol/L $_L$-glutamine (purchased from HyClone, USA), 1× nonessential amino acids (purchased from HyClone, USA), 100 μg/ml streptomycin and 100 U/ml penicillin. All tumor cell lines are incubated in an incubator with temperature of 37° C., $CO_2$ concentration of 5% and humidity of 95%. Medium used for culturing the tumor cell lines are renewed once in two days.

While subculturing, the tumor cell lines are centrifuged at 1000 rpm for 5 min to remove supernatants, followed by mixing with fresh medium. The tumor cell lines preferably have a concentration of $1 \times 10^5$-$1 \times 10^6$ cells/ml in 10 cm culturing dishes.

The culturing dishes 80-90% of bottom areas covered by the tumor cells are used in this experiment. Discolored medium is removed, 8 ml of PBS solution is used to wash the tumor cells and Trypsin/EDTA is added into the culturing dishes for 1-3 min. After the tumor cells dissociate with walls of the culturing dishes by slightly vortexing, the tumor cells are resuspended with prewarmed medium. The tumor cells are collected into centrifuge tubes, followed by centrifugation at 1500 rpm for 10 min. Supernatants are removed and the tumor cells are resuspended in medium containing FBS. 20 μl of the tumor cells are collected, and 20 μl of trypan blue is added to the tumor cells for staining. The stained tumor cells are collected in cell counters, and numbers of the stained tumor cells are counted under microscope. Only the tumor cells with viability over 95% are suitable for the following experiments.

Concentrations of the tumor cell lines are adjusted to $1 \times 10^5$ cells/ml by medium containing FBS. 100 μl of the tumor cell lines with a concentration of $1 \times 10^4$ cells/well are inoculated in a 96-well plate. The tumor cells lines are overnight cultured in an incubator with temperature of 37° C. and $CO_2$ concentration of 5%.

After culturing for 24 hours, the crude extracts of *Taiwanofungus camphorates* are added into each well of the 96-well plate. The tumor cells lines are overnight cultured in an incubator with temperature being 37° C. and $CO_2$ concentration being 5%.

After culturing for 24 hours, medium is removed, and the tumor cells are washed by a PBS solution. 0.5 mg/ml MTT containing-fresh medium is added into each well of the 96-well plate. The tumor cells react with MTT for 4 hours in the incubator (37° C., 5% $CO_2$). Absorbance of 570 nm of the tumor cells in each well is detected.

Figure 1A:
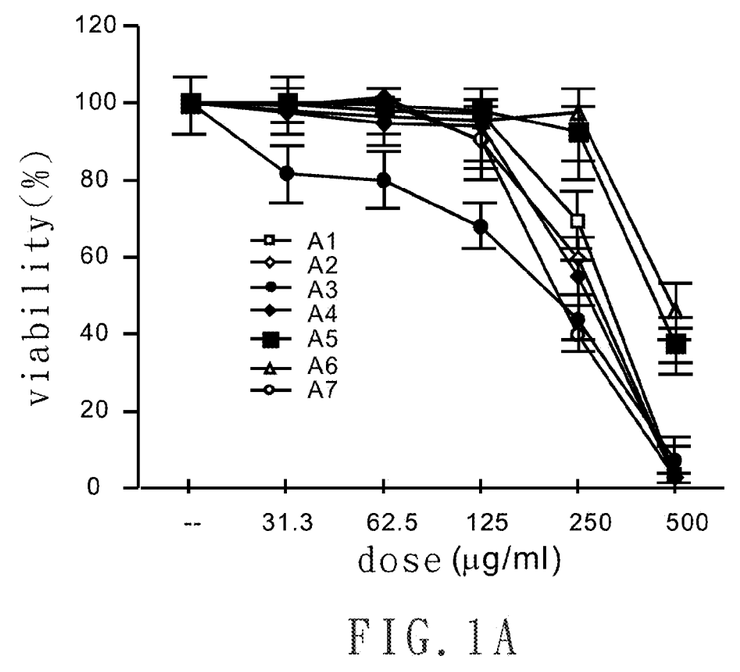
FIG. 1A depicts a line chart showing influences of the formula of the invention on viability of mice sarcoma cells treated with the formula of the invention.

FIG. 1A depicts the line chart of viability of mice sarcoma cells treated with the crude extracts shown in Table 1. Viability is computed as followed:

Viability (%)=(Absorbance of a testing set/Absorbance of a control set)×100%

Referring to FIG. 1A, compared to single extracts of *Taiwanofungus camphorates, Ganoderma lucidum* and *Glycyrrhiza uralensis* Fisch (line of A5-A7), mixed extracts of the formula of the invention (line of A1-A4) show a significant inhibition on viability of mice sarcoma cells.

Figure 1B:
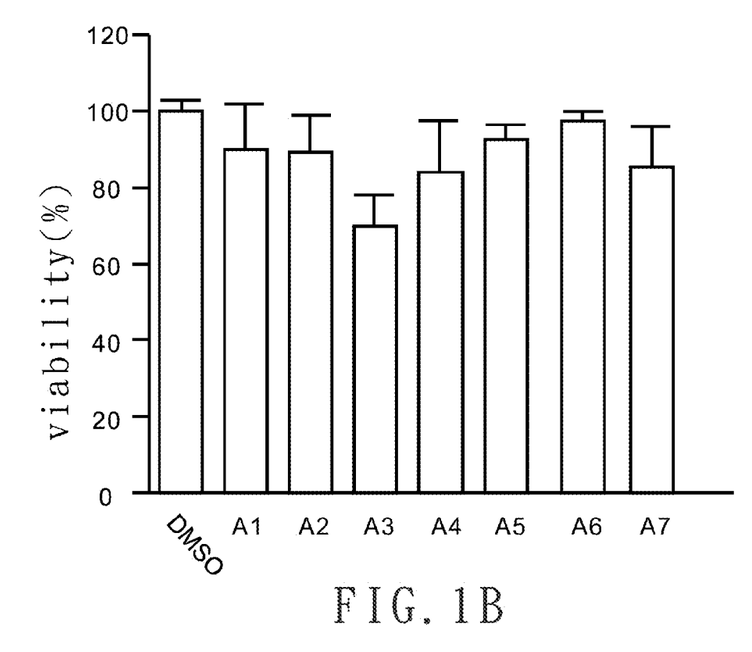
FIG. 1B depicts a bar chart showing influences of 125 µl/ml of the formula of the invention on viability of mice sarcoma cells treated with the formula of the invention and the control (DMSO).

Referring to FIG. 1B, a bar chart showing viability of mice sarcoma cells treated with 125 μl/ml of the crude extracts shown in Table 1, group A3 shows a significant inhibition on viability of mice sarcoma cells.

Figure 2A:
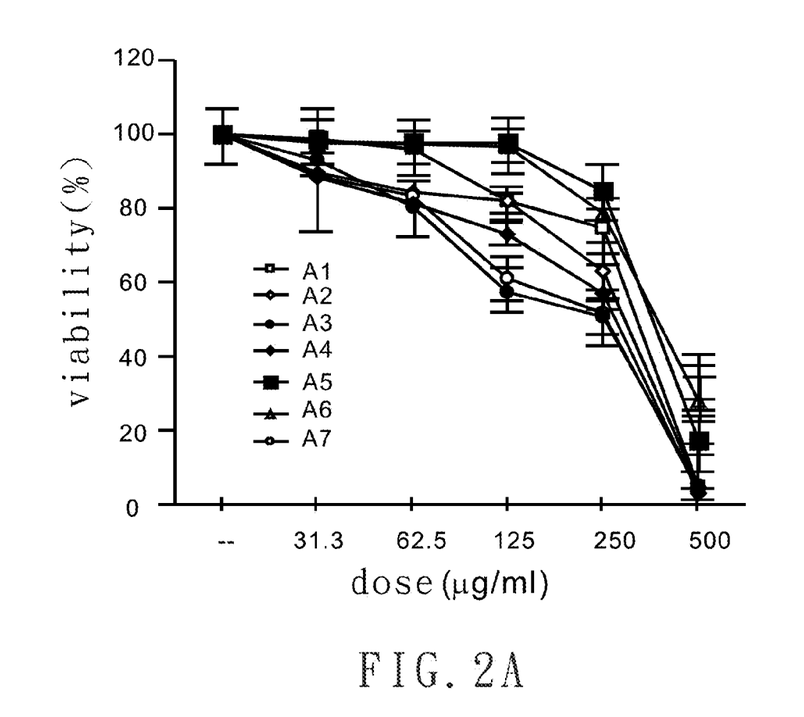
FIG. 2A depicts a line chart showing influences of the formula of the invention on viability of human lung tumor cells treated with the formula of the invention.
Figure 2B:
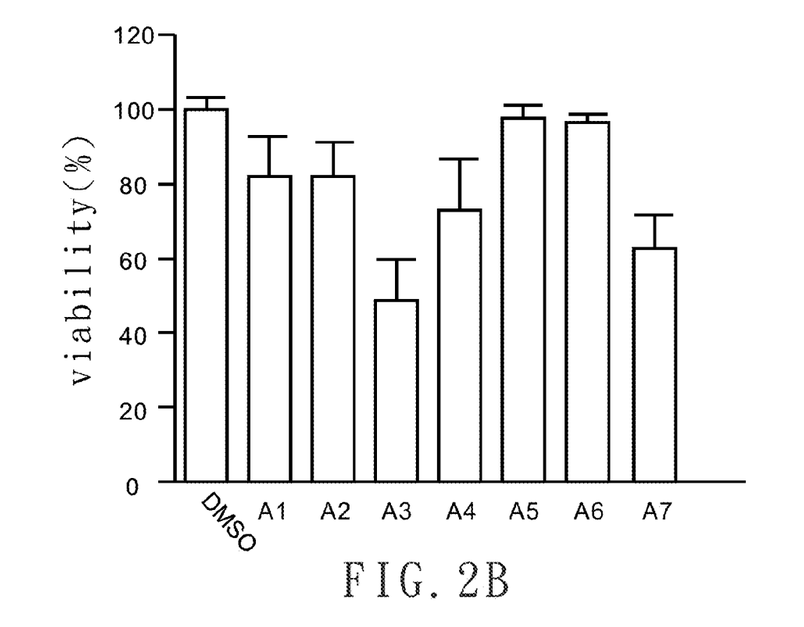
FIG. 2B depicts a bar chart showing influences of 125 µl/ml of the formula of the invention on viability of human lung tumor cells treated with the formula of the invention and the control (DMSO).
Figure 3A:
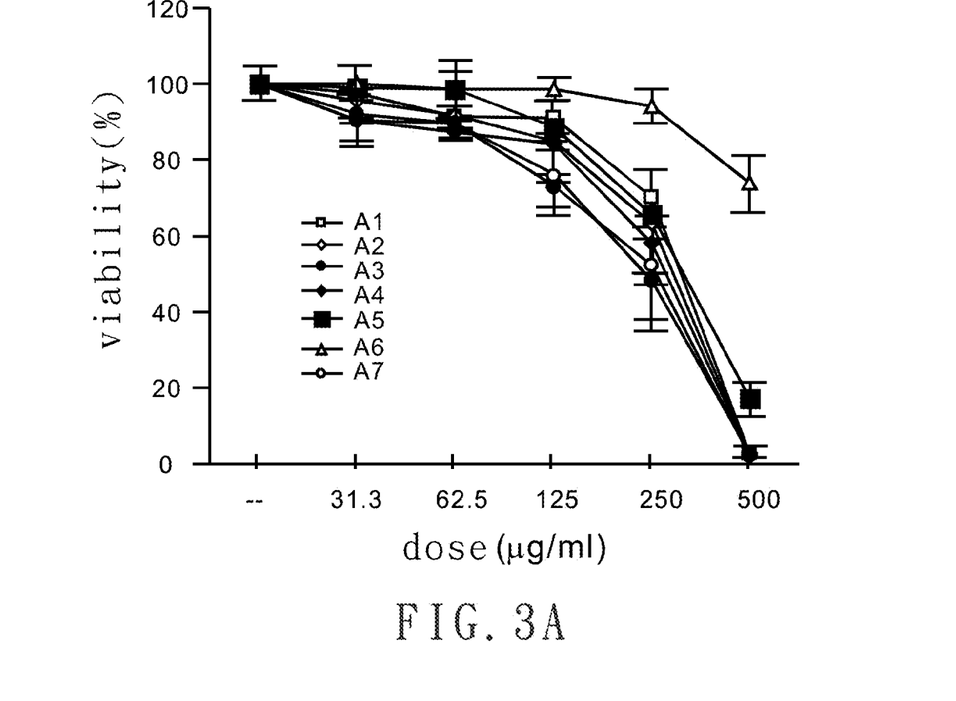
FIG. 3A depicts a line chart showing influences of the formula of the invention on viability of human hepatic tumor cells treated with the formula of the invention.
Figure 3B:
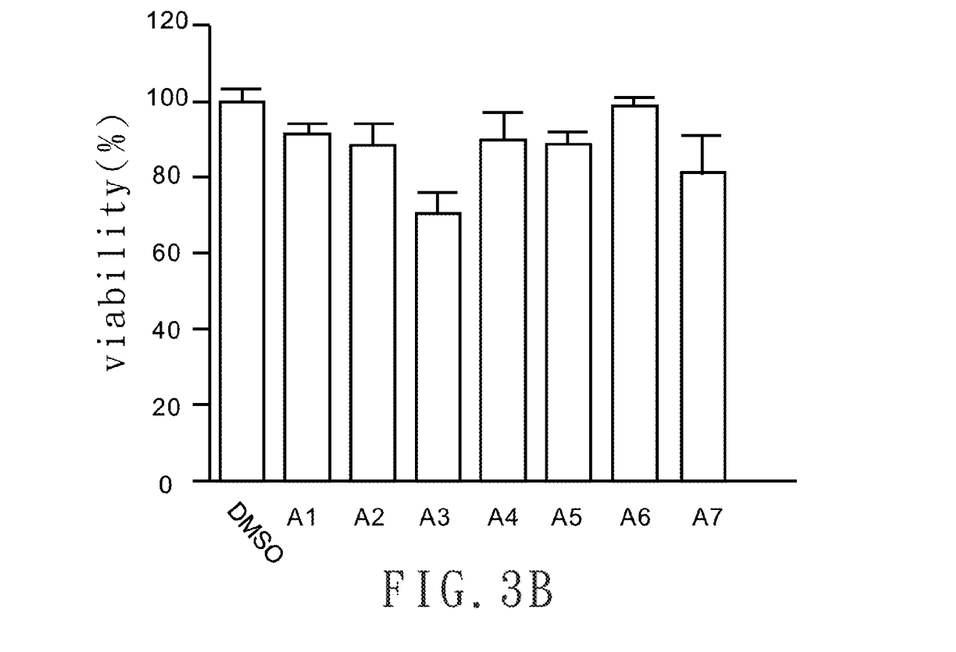
FIG. 3B depicts a bar chart showing influences of 125 µl/ml of the formula of the invention on viability of human hepatic tumor cells treated with the formula of the invention and the control (DMSO).
Figure 4A:
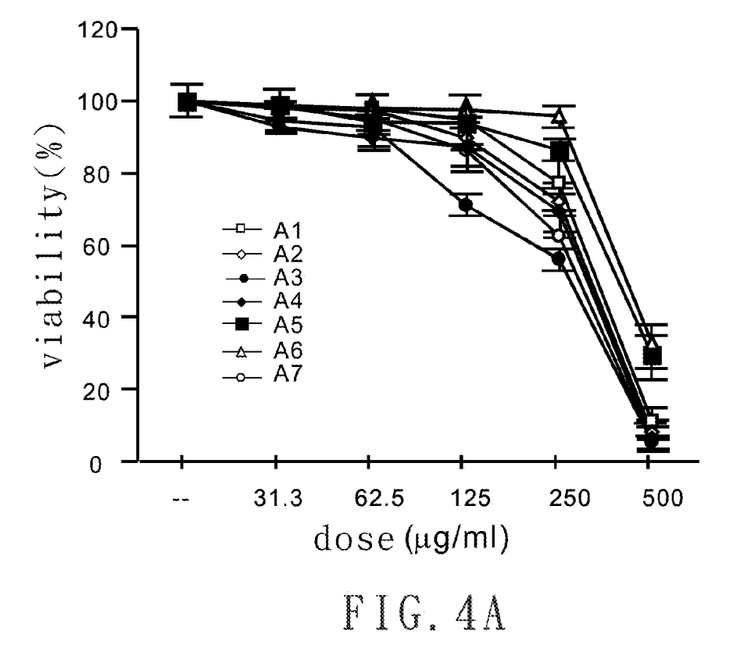
FIG. 4A depicts a line chart showing influences of the formula of the invention on viability of human colorectal tumor cells treated with the formula of the invention.
Figure 4B:
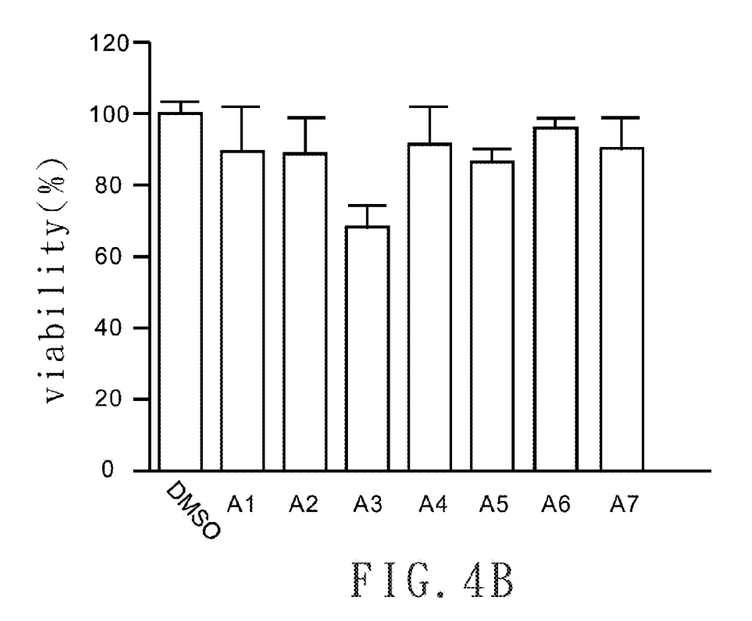
FIG. 4B depicts a bar chart showing influences of 125 µl/ml of the formula of the invention on viability of human colorectal tumor cells treated with the formula of the invention and the control (DMSO).
Figure 5A:
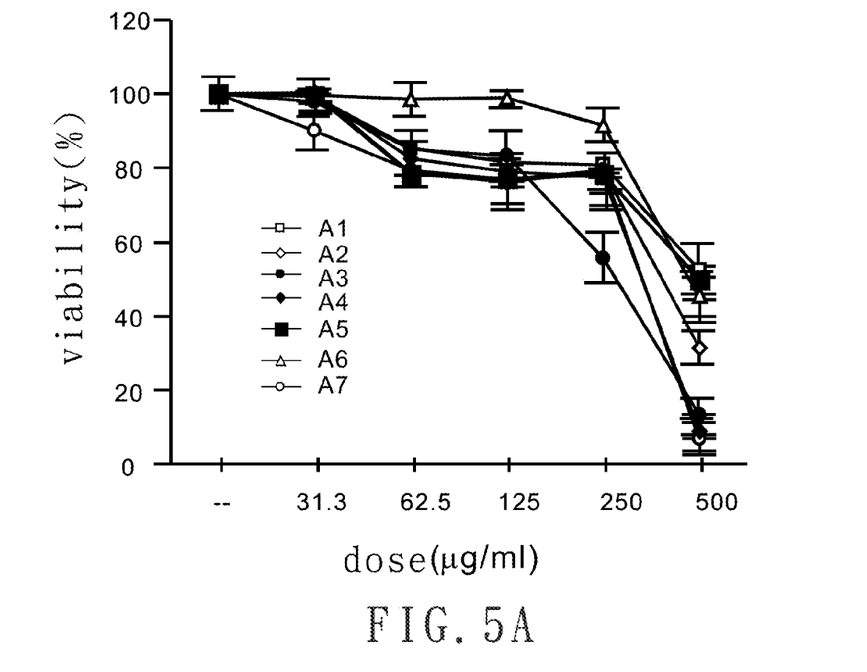
FIG. 5A depicts a line chart showing influences of the formula of the invention on viability of human breast tumor cells treated with the formula of the invention.
Figure 5B:
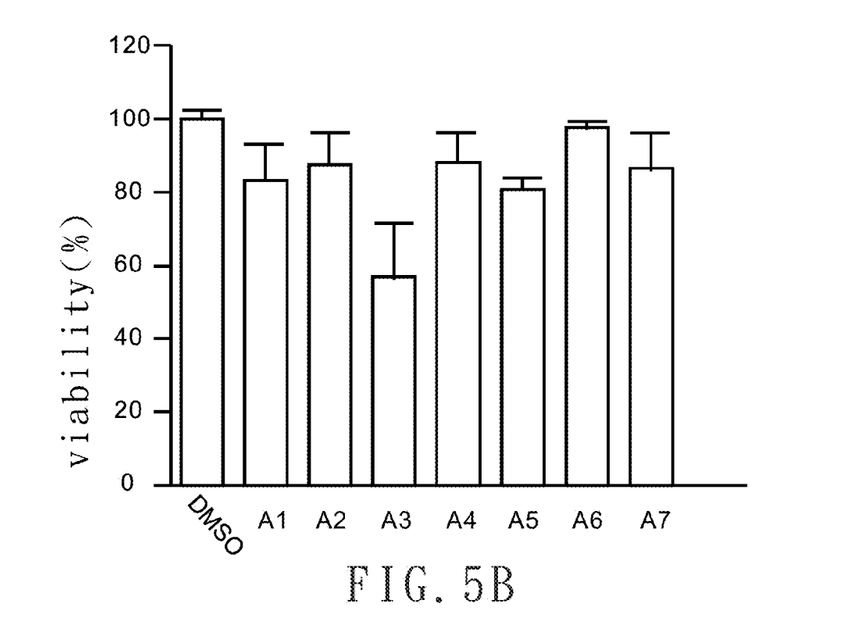
FIG. 5B depicts a bar chart showing influences of 125 µl/ml of the formula of the invention on viability of human breast tumor cells treated with the formula of the invention and the control (DMSO).

Moreover, compared to single extracts of *Taiwanofungus camphorates, Ganoderma lucidum* and *Glycyrrhiza uralensis* Fisch (A5-A7), mixed extracts of the formula of the invention (A1-A4) show a significant inhibition on viability of human lung tumor cells (as shown in FIGS. 2A and 2B), human hepatic tumor cells (as shown in FIGS. 3A and 3B), human colorectal tumor cells (as shown in FIGS. 4A and 4B) and human breast tumor cells (as shown in FIGS. 5A and 5B).

(C) In Vivo Pharmacological Study of the Formula of the Invention

Specific-pathogen free Balb/C male mice (8 week-old, weight 20-25 g) purchased from the animal center of the national Cheng Kung University are used in this experiment. The mice are housed in an animal room with constant temperature of 25±1° C. where is kept on a 12-hours light and 12-hours dark cycle. The mice are housed and kept on free diet and water, which provided by the animal center of the national Cheng Kung University.

The sarcoma cells, such as the S-180 cell lines purchased from the Food Industry Research and Development Institute in Taiwan are diluted to a concentration of $5 \times 10^6$ cells/ml by a saline solution. The diluted sarcoma cells are applied to a back portion of the mice via subcutaneous injection.

The crude extract of group A3 is diluted into diet with a ratio of 0.25% (group C2), 0.5% (group C3) and 1% (group C4). Group C1 is a control set without the crude extract. The mice are kept on free diet for 30 days. Tumor size is calculated with an equation of length×width×height×0.45. Viability of mice is recorded.

Figure 6A:
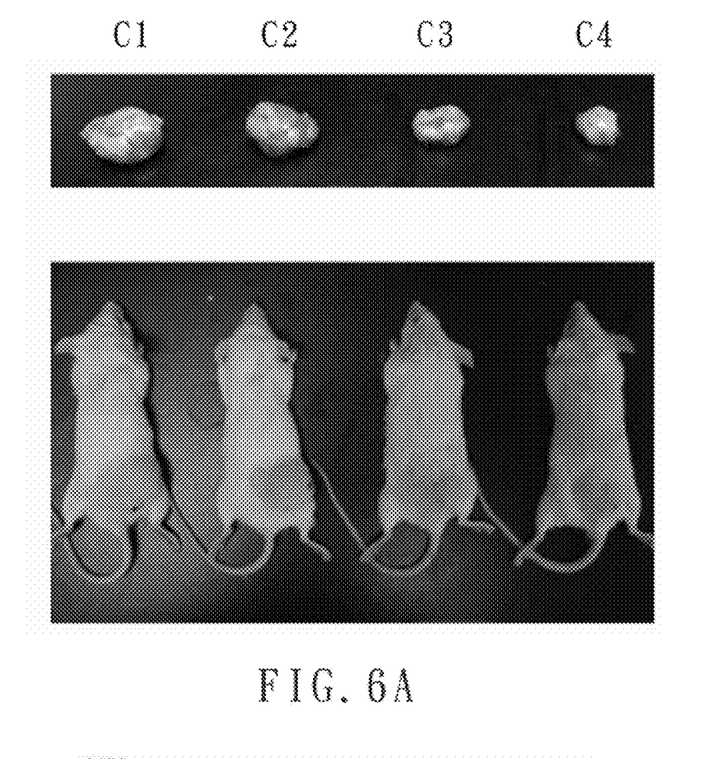
FIG. 6A depicts photos showing influences of the formula of the invention on tumor sizes in sacrificed animals treated with different doses of the formula of the invention and the control (untreated animal) for 30 days.
Figure 6B:
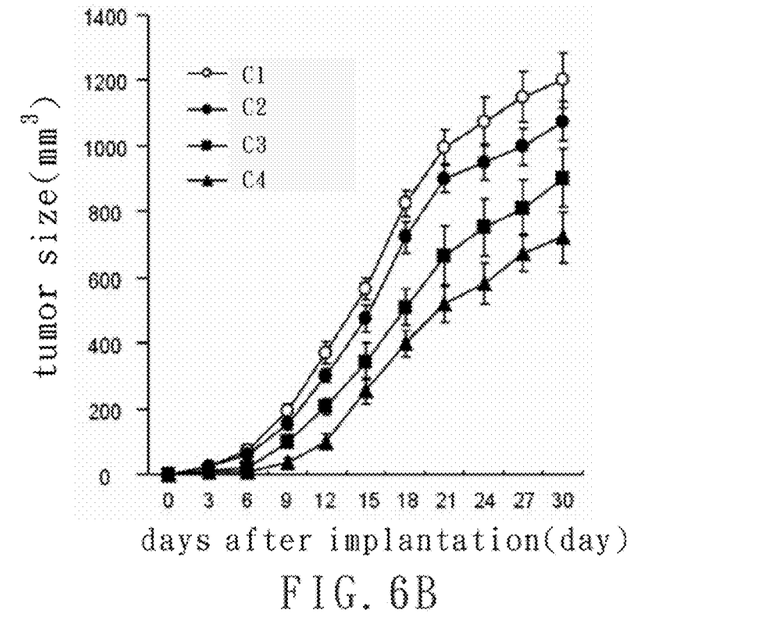
FIG. 6B depicts a line chart showing influences of the formula of the invention on tumor sizes in animals treated with different doses of the formula of the invention and the control (untreated animal) within 30 days.

Referring to FIGS. 6A and 6B, additions of the crude extracts of the invention (group C2-C4) into diet show a significant decreasing on tumor size and tumor growth. Furthermore, the inhibition of tumor growth shows a positive correlation with the concentration of crude extracts of the invention.

Figure 7:
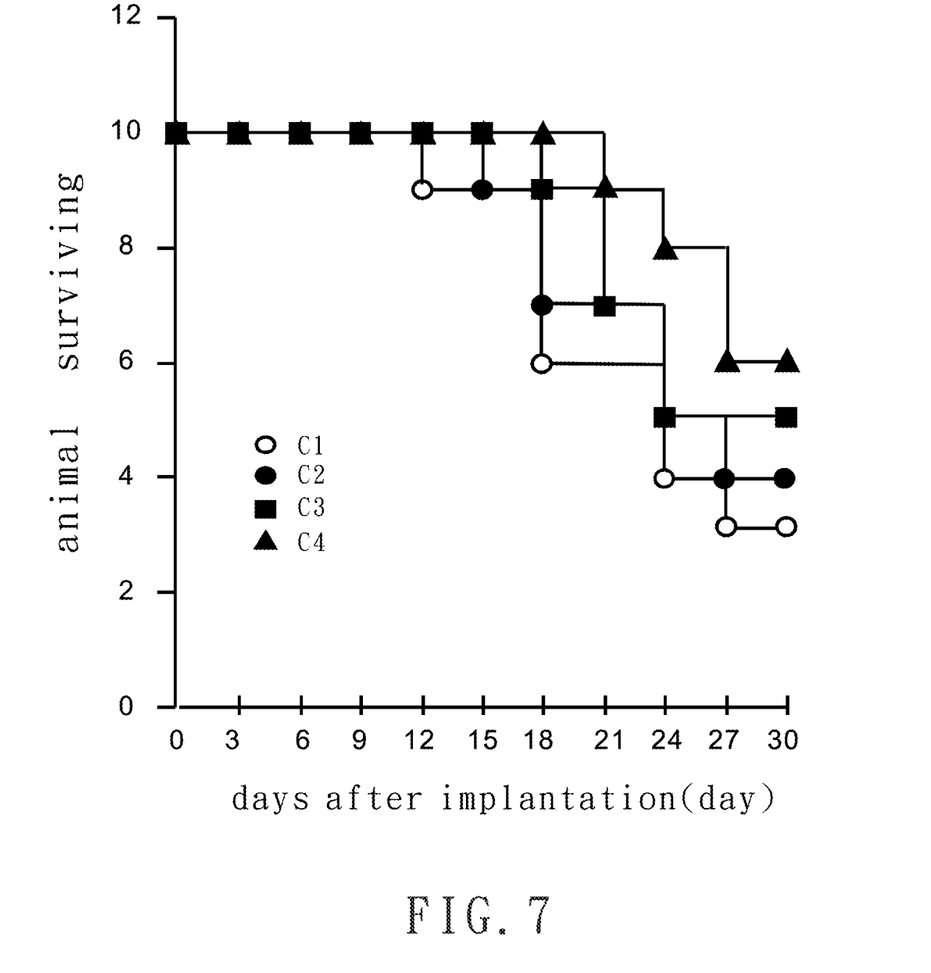
FIG. 7 depicts a line chart showing influences of the formula of the invention on mortality of animals treated with different doses of the formula of the invention and the control (untreated animal) within 30 days.

Referring to FIG. 7, the crude extracts show a significant decreasing on mortality of mice caused by inoculation of mice sarcoma cells.

In summary, the formula of the invention is capable to serve as an active ingredient effectively suppressing viability of tumor cells.

Furthermore, compared to the single extracts of *Taiwanofungus camphorates, Ganoderma lucidum* and *Glycyrrhiza uralensis* Fisch, the formula of the invention shows a significant inhibition on viability of tumor cells. In accordance with combination of the raw materials, the side effects caused by long-term administration of *Taiwanofungus camphorates* can be effectively reduced.

Moreover, the medication of suppressing viability of tumor cells of the invention comprises the formula of the invention capable to serve as an active ingredient effectively suppressing viability of tumor cells. By virtue of the formula of the invention, induced cytotoxicity and apoptosis in tumor cells can prevent tumor from proliferation and metastasis.

Although the invention has been described in detail with reference to its presently preferable embodiment, it will be understood by one of ordinary skill in the art that various modifications can be made without departing from the spirit and the scope of the invention, as set forth in the appended claims.

The invention claimed is:

1. A formula comprising: 27.3-50.0 wt % of an ethanol extract of *Taiwanofungus camphorates*, 27.3-40.0 wt % of an ethanol extract of *Ganoderma lucidum* and 16.7-45.4 wt % of an ethanol extract of *Glycyrrhiza uralensis* Fisch.

2. The formula as claimed in claim 1, wherein the weight percentage the ethanol extract of *Taiwanofungus camphorates* is 30.8% by weight of the formula.

3. The formula as claimed in claim 1, wherein the weight percentage of the ethanol extract of *Ganoderma lucidum* is 30.8% by weight of the formula.

4. The formula as claimed in claim 1, wherein the weight percentage of the ethanol extract of *Glycyrrhiza uralensis* Fisch is 38.5% by weight of the formula.

5. The formula as claimed in claim 1, wherein the weight percentages of the ethanol extract of *Taiwanofungus camphorates*, the ethanol extract of *Ganoderma lucidum* and the ethanol extract of *Glycyrrhiza uralensis* Fisch are 30.8%, 30.8% and 38.5% by weight of the formula, respectively.

6. The formula as claimed in claim 1, wherein the ethanol extract of *Taiwanofungus camphorates* is extracted from a fruit body of *Taiwanofungus camphorates*.

7. A medication of suppressing tumor cell proliferation, comprising:
the formula as defined in claim 1; and
a medical acceptable excipient.

* * * * *